(12) United States Patent
Goldstein et al.

(10) Patent No.: US 10,449,127 B2
(45) Date of Patent: Oct. 22, 2019

(54) MICROCAPSULES COMPRISING BLACK PIGMENTS

(75) Inventors: Danny Goldstein, Kibbutz Dafna (IL); Yuri Yasman, Carmiel (IL); Olga Privalova, Kibbutz LeHavot HaBashan (IL); Lior Benaltabet, Kibbutz Dafna (IL)

(73) Assignee: Tagra Biotechnologies, Ltd., Natania (IL)

( * ) Notice: Subject to any disclaimer, the term of this patent is extended or adjusted under 35 U.S.C. 154(b) by 0 days.

(21) Appl. No.: 14/118,266

(22) PCT Filed: May 16, 2012

(86) PCT No.: PCT/IL2012/000192
§ 371 (c)(1),
(2), (4) Date: Nov. 18, 2013

(87) PCT Pub. No.: WO2012/156965
PCT Pub. Date: Nov. 22, 2012

(65) Prior Publication Data
US 2014/0335138 A1    Nov. 13, 2014

Related U.S. Application Data
(60) Provisional application No. 61/486,413, filed on May 16, 2011.

(51) Int. Cl.
| | | |
|---|---|---|
| *A61K 8/11* | (2006.01) | |
| *B01J 13/12* | (2006.01) | |
| *A61Q 1/10* | (2006.01) | |
| *C09C 1/48* | (2006.01) | |
| *C09C 1/56* | (2006.01) | |
| *C09C 3/10* | (2006.01) | |
| *C09C 1/00* | (2006.01) | |
| *C09C 1/24* | (2006.01) | |
| *A61Q 1/02* | (2006.01) | |
| *A61Q 1/06* | (2006.01) | |
| *A61Q 1/08* | (2006.01) | |
| *A61K 8/73* | (2006.01) | |
| *A61K 8/81* | (2006.01) | |
| *A61K 8/02* | (2006.01) | |
| *A61K 8/19* | (2006.01) | |

(52) U.S. Cl.
CPC ............ *A61K 8/11* (2013.01); *A61K 8/0241* (2013.01); *A61K 8/19* (2013.01); *A61K 8/731* (2013.01); *A61K 8/8147* (2013.01); *A61K 8/8152* (2013.01); *A61Q 1/02* (2013.01); *A61Q 1/06* (2013.01); *A61Q 1/08* (2013.01); *A61Q 1/10* (2013.01); *B01J 13/12* (2013.01); *C09C 1/0081* (2013.01); *C09C 1/24* (2013.01); *C09C 1/48* (2013.01); *C09C 1/56* (2013.01); *C09C 3/10* (2013.01); *A61K 2008/115* (2013.01); *A61K 2800/412* (2013.01); *A61K 2800/43* (2013.01); *A61K 2800/624* (2013.01); *A61K 2800/651* (2013.01); *C01P 2004/52* (2013.01); *C01P 2004/61* (2013.01); *C01P 2006/10* (2013.01); *C01P 2006/11* (2013.01)

(58) Field of Classification Search
CPC ...... A61K 8/11; A61K 8/8152; A61K 8/8147; A61K 8/731; A61Q 1/08; A61Q 1/06; A61Q 1/02; A61Q 1/10; C09C 1/24; C09C 1/48

See application file for complete search history.

(56) References Cited

U.S. PATENT DOCUMENTS

| | | | |
|---|---|---|---|
| 2004/0146641 A1 | 7/2004 | Hobbs et al. | |
| 2005/0154083 A1 | 7/2005 | Hobbs et al. | |
| 2006/0051425 A1 | 3/2006 | Kvitnitsky et al. | |
| 2009/0023818 A1 | 1/2009 | Rodier et al. | |
| 2009/0311295 A1 | 12/2009 | Mathiowitz et al. | |
| 2010/0160492 A1* | 6/2010 | Liang | C09D 7/80 523/205 |
| 2010/0254929 A1* | 10/2010 | Raineau | A61K 8/31 424/70.7 |
| 2016/0008237 A1* | 1/2016 | Goldstein | A61K 8/29 424/401 |

FOREIGN PATENT DOCUMENTS

| | | | | |
|---|---|---|---|---|
| CN | 1764691 | 4/2006 | | |
| CN | 101309746 | 11/2008 | | |
| EP | 2277982 | 1/2011 | | |
| JP | 63-060914 | 3/1988 | | |
| JP | 08-227611 | 9/1996 | | |
| JP | 2006-517602 | 7/2006 | | |
| JP | 2008-519017 | 6/2008 | | |
| JP | 2009-504402 | 2/2009 | | |
| JP | 2009-203212 | 9/2009 | | |
| WO | WO 01/35933 | 5/2001 | | |
| WO | WO 2004/065475 | 8/2004 | | |
| WO | WO 2007/023495 | 3/2007 | | |
| WO | WO 2009/138978 | 11/2009 | | |
| WO | WO-2009138978 A2 * | 11/2009 | ........... | A61K 8/0212 |
| WO | WO 2009138978 A2 * | 11/2009 | ........... | A61K 8/0212 |
| WO | WO 2011/006657 | 1/2011 | | |
| WO | WO 2012/156965 | 11/2012 | | |

OTHER PUBLICATIONS

Evonik brochure 2015 [downloaded on Jun. 20, 2015 from the website http://eudragit.evonik.com/product/eudragit/en/products-services/eudragit-products/sustained-release-formulations/rs-100/Pages/default.aspx].*
Cosmetic Ingredient Review 2008 [downloaded on Jun. 20, 2015 from the website http://www.cir-safety.org/sites/default/files/115_buff3e_suppl.pdf].*
Gwinn et al., "Nanoparticles: Health Effects—Pro and Con", Environmental Health Perspectives 114: 1818-1825 (2006).*

(Continued)

*Primary Examiner* — Mina Haghighatian (57) ABSTRACT

Monolayered microcapsules comprising a black pigment and cosmetic formulations comprising them are provided for use particularly in mascara and eye liner formulations. The black pigment may be carbon black, black iron oxide, or both.

14 Claims, 4 Drawing Sheets

(56) References Cited

OTHER PUBLICATIONS

Nowack et al., "Occurrence, behavior and effects of nanoparticles in the environment", Environmental Pollution 150: 5-22 (2007).*
Evonik brochure 2015.*
Tiarks et al., "Encapsulation of Carbon Black by Miniemulsion Polymerization", Macromol. Chem. Phys 202: 51-60 (2001).*
International Search Report and the Written Opinion dated Jan. 10, 2013 From the International Searching Authority Re. Application No. PCT/IL2012/000192.
International Preliminary Report on Patentability dated Nov. 28, 2013 From the International Bureau of WIPO Re. Application No. PCT/IL2012/000192.
Notification of Office Action and Search Report dated Mar. 23, 2015 From the State Intellectual Property Office of the People's Republic of China Re. Application No. 201280035127.6 and Its Translation Into English.
Translation Dated Dec. 30, 2015 of Notification of Office Action dated Dec. 10, 2015 From The State Intellectual Property Office of the People's Republic of China Re. Application No. 201280035127.6.
Notice of Reason for Rejection dated Jan. 29, 2016 From the Japanese Patent Office Re. Application No. 2014-510945 and Its Translation Into English.
Notification of Office Action dated Dec. 10, 2015 From The State Intellectual Property Office of the People's Republic of China Re. Application No. 201280035127.6.
Notice of Reason for Rejection dated Sep. 27, 2016 From the Japanese Patent Office Re. Application No. 2014-510945 and Its Machine Translation Into English.
Communication Pursuant to Article 94(3) EPC dated Apr. 4, 2017 From the European Patent Office Re. Application No. 12730274.3. (6 Pages).
Examination Report Under Sections 12 & 13 of the Patents Act, 1970 and the Patents Rules, 2003 dated Feb. 6, 2018 From the Government of India, Intellectual Property India, Patents, Designs, Trade Marks Geographical Indications Re. Application No. 2378/MUMNP/2013. (6 Pages).
Summons to Attend Oral Proceedings Pursuant to Rule 115(1) EPC dated Nov. 13, 2018 From the European Patent Office Re. Application No. 12730274.3. (6 Pages).

\* cited by examiner

MICROCAPSULES COMPRISING BLACK PIGMENTS

RELATED APPLICATIONS

This application is a National Phase of PCT Patent Application No. PCT/IL2012/000192 having International filing date of May 16, 2012, which claims the benefit of priority under 35 USC § 119(e) of U.S. Provisional Patent Application No. 61/486,413 filed on May 16, 2011. The contents of the above applications are all incorporated by reference as if fully set forth herein in their entirety.

FIELD OF THE INVENTION

The present invention relates to microcapsules comprising black pigments and to topical compositions comprising them, particularly for use in cosmetics, more particularly for use in mascara and eye liner formulations.

BACKGROUND OF THE INVENTION

The most popular black pigments in cosmetic products nowadays are carbon black and iron oxide black. Black iron oxide pigment, also known as ferrous ferric oxide ($Fe_3O_4$), consists of particles with diameters between about 1 and 100 nanometers. It has no known health hazards and is considered non-toxic. It is more opaque and less toxic than other black pigments.

Carbon black pigment is produced by the incomplete combustion of hydrocarbon gas or oil. It is an ultra black pigment, providing the most authentic black shades available. The benefits of carbon black for use in cosmetics and particularly in mascaras include less clumping, less beading, less buildup, better lash separation and better lash curling. Since carbon black is lighter with more color effect at low use concentrations, final formulations offer maximum cosmetic performance without caking and buildup.

However, carbon black has not been permitted for cosmetic use in the U.S. from 1976 to 2004. In 2004 the U.S. Food and Drug Administration (FDA) approved the use in cosmetics of one form of carbon black: high purity furnace black (one of the five types of carbon black which have been produced). The FDA named the allowed colorant D&C Black #2 to emphasize that the material is subject to batch certification.

In addition, carbon black is very difficult to handle during the process of manufacturing formulations. It consists of fine amorphous particles having an average primary particle size as small as 0.05 to 0.5 µm. Due to the fine primary particle size, carbon black particles tend to heavily aggregate and can be difficult to disperse uniformly in vehicles or resin compositions. In addition, carbon black particles have a very low bulk density (about 0.1 g/cm$^3$) and, accordingly, can easily become airborne and contaminate the working environment.

Pigments, especially carbon black, present problems to customers trying to handle and disperse these products. Customers desire to have a product which is dust free, can be easily handled in conventional material transferring equipment and have the same product in a form that will easily disperse in the host formulation. Additionally, carbon black lacks significant surface functional groups, which means that the particles are hard to wet and therefore difficult to disperse.

Achieving an adequate dispersion involves imparting enough energy in the system to overcome attractive forces between particles without putting much energy in the system that can destroy or change the desired properties of the formulation. Achieving dispersions of particulate matter, and in particular carbon black dispersions, remains the domain of experience and know how.

The primary particle size of a carbon black particle determines, to a large extent, its degree of dispersibility. The smaller the primary particle the higher the surface area, resulting in more area to wet and thus requiring more energy than a carbon black particle having lower surface area. Additionally, as the carbon black aggregate becomes smaller there is a higher volume concentration of carbon black at the same weight loading (compared to particles having larger aggregates) resulting in smaller inter-aggregate distances and, consequently, greater attractive forces to overcome.

It would be beneficial to provide carbon black in an encapsulated form that would increase the safety of use, avoid dustiness during manufacturing of the composition, and improve dispersion of carbon black in the composition and will not be considered as a nanomaterial (1-100 nanometer).

U.S. Pat. No. 5,286,291 discloses pigments containing carbon black and having improved abrasion resistance. WO 2010/085689 discloses antimicrobial carbon black dispersions. U.S. Pat. No. 7,300,512 discloses a method of making pigment dispersion containing a carrier such as castor oil or vegetable wax, wherein the pigment is optionally black iron oxide.

U.S. Pat. Nos. 6,932,984 and 7,838,037 assigned to the same applicant of the present application disclose a method for microencapsulation of substances by the solvent removal method using non-chlorinated solvents. The method is based on physical processes only which do not cause any change of original physical and/or chemical properties, biological activity, and safety of raw materials during the process. This method affords physical stability of the microcapsules, high ability to entrap the active agents, protection of the active agents inside the microcapsules, and prevention of the diffusion of the microencapsulated active agents to the external water phase in a water-based preparation. In U.S. Pat. No. 7,838,037 the resulting microcapsules are double layer and triple layer microcapsules. WO 2009/138978 of the same applicant discloses cosmetic compositions comprising double layer microcapsules which contain black iron oxide with additional iron oxides.

DETAILED DESCRIPTION OF THE INVENTION

Among conventional black pigments, carbon black exhibits excellent blackness. Carbon black powder consists of fine amorphous particles exhibiting average particle size as small as 0.05 to 0.5 µm. Special color effects can be achieved by incorporation of carbon black into pigments. Carbon black (D&C Black #2) is approved by FDA for use in eyeliner, mascara, eye shadow, lipstick, blush, make up and foundation.

In order to get full color tone out of carbon black it is of paramount importance that a good dispersion is made. However, it is very difficult to disperse carbon black uniformly in formulations. Carbon black particle size is directly related to the surface area of the pigment and influences its color, rheology, dispersion and electrical conductivity in the formulation. Carbon black particles tend to heavily aggregate. It can easily become airborne and contaminate work environments (bulk density of 0.1 g/cm$^3$).

The present invention provides monolayered microcapsules comprising a core of a black pigment and a shell of a wall-forming polymeric material selected from a polyacrylate, a polymethacrylate, a cellulose ether, a cellulose ester, or a combination thereof, wherein the microcapsules do not contain a plasticizer (the plasticizer would cause softening of the wall-forming polymers).

According to certain embodiments, the black pigment is carbon black. Contrary to known carbon black particles with size as small as 0.05 to 0.5 μm, the carbon black microcapsules of the present invention have a size ranging from about 1 to about 100 μm, about 1 to about 90 μm, about 1 to about 80 μm, about 1 to about 70 μm, about 1 to about 60 μm, about 1 to about 50 μm, about 30 to about 50 μm, about 34 to about 40 μm, about 1 to about 40 μm, about 1 to about 30 μm, about 1 to about 20 μm, about 1 to about 10 μm, about 1 to about 5 μm, or about 1 to about 3 μm, preferably about 1 to 2 μm. For example, microcapsules with mean particle size of 1.5 μm or 34 μm have a surface area of 4-5 m$^2$/g and 0.2-0.4 m$^2$/g, respectively. The particle size of the microcapsules according to the present invention provides increased safety and greater ease in handling the pigment during the process for manufacturing cosmetic compositions.

According to certain embodiments, the amount of carbon black in the microcapsules of the invention is within a range selected from about 25 to about 95%, about 30 to about 90%, about 40 to about 90%, about 50 to about 90%, about 60 to about 90%, about 70 to about 90%, about 80 to about 90%, or about 85 to about 90%, preferably about 90%, by weight.

According to certain embodiments, the black pigment is black iron oxide. Contrary to the microcapsules containing iron oxides disclosed in U.S. Pat. Nos. 6,932,984, 7,838,037 and WO 2009/138978, the microcapsules of the present invention are monolayer microcapsules and they do not contain plasticizers. According to certain embodiments, the amount of black iron oxide in the microcapsules of the invention is within a range selected from about 50 to about 95%, about 60 to about 95%, about 75 to about 95%, about 80 to about 95%, about 80 to about 90%, or about 90 to about 95%, preferably about 80%, 90% or 95%, by weight.

According to certain embodiments, the black pigment is a mixture of carbon black and black iron oxide, wherein the ratio between the carbon black and black iron oxide is in a range of from 1:20 to 20:1, respectively. In certain embodiments the ratio between the carbon black and black iron oxide is 1:1, 1:2, 1:3, 1:4, 1:5, 1:6, 1:7, 1:8, 1:9, 1:10, 1:11, 1:12, 1:13, 1:14, 1:15, 1:16, 1:17, 1:18, 1:19, 1:20, 20:1, 19:1, 18:1, 17:1, 16:1, 15:1, 14:1, 13:1, 12:1, 11:1, 10:1, 9:1, 8:1, 7:1, 6:1, 5:1, 4:1, 3:1, 2:1, 2:3, or 3:2, respectively. The total amount of black pigment ranges from about 50 to about 90%, about 60 to about 90%, about 75 to about 90%, about 80 to about 90%, preferably about 80% or 90%, by weight.

The term "microcapsule", as used herein, refers to a spherical microparticle consisting of a polymeric shell serving as a wall-forming material and encapsulated black pigment located within the core of the microcapsule. Microcapsules are distinct from microspheres, which consist of spherical homogeneous granules of the active substance dispersed in a polymer and are, in strict sense, spherically empty particles.

The term "wall-forming polymer" refers to a polymer or a combination of two or more different polymers as defined herein, which form a component of the external wall or layer or shell of the microcapsules. The term "polymer shell" refers to a polymer layer containing the wall-forming polymer(s).

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 μm" is intended to mean "about 40 μm".

As used herein, numerical ranges preceded by the term "about" should not be considered to be limited to the recited range. Rather, numerical ranges preceded by the term "about" should be understood to include a range accepted by those skilled in the art for any given element in microcapsules or formulations according to the present invention.

The term "about" as used herein means within an acceptable error range for a particular value as determined by one of ordinary skill in the art, which will depend in part on how the value is measured or determined, i.e., the limitations of the measurement system. For example, "about" can mean a range of up to 10%, more preferably up to 5%, and still more preferably up to 1% of a given value. Where particular values are described in the application and claims, unless otherwise stated, the meaning of the term "about" within an acceptable error range for the particular value should be assumed.

The method used for the preparation of the microcapsules of the invention as described hereinafter is based on the microencapsulation solvent removal method disclosed by the applicant of the present application in the above-mentioned U.S. Pat. Nos. 6,932,984 and 7,838,037. According to this technology, the active ingredient is found in the core of the microcapsule. This technique seals each micro-capped ingredient from chemical and cross-link reactions, degradation, color change or loss of potency during production and for extended periods in storage.

However, in contrast to the microcapsules of U.S. Pat. Nos. 6,932,984, 7,838,037 and WO 2009/138978, the microcapsules of the present invention do not contain plasticizers, which cause the softening of the wall-forming polymers, resulting in the release of their content upon application to the skin. The microcapsules of the present invention are formulated to retain the black pigment, and not to release it upon application. Furthermore, the encapsulation does not change the color of the pigments; rather the encapsulated black pigments have an intense black color.

It was surprisingly found, according to the present invention, that application of the technology developed by the applicant for the microencapsulation of black pigments solves a problem in the cosmetic industry while handling nanoparticles of said pigments.

The microcapsules of the invention have a particle size within a range selected from about 1 to about 100 μm, about 1 to about 90 μm, about 1 to about 80 μm, about 1 to about 70 μm, about 1 to about 60 μm, about 1 to about 50 μm, about 30 to about 50 μm, about 34 to about 40 μm, about 1 to about 40 μm, about 1 to about 30 μm, about 1 to about 20 μm, about 1 to about 10 μm, about 1 to about 5 μm, or about 1 to about 3 μm. In preferred embodiments, the mean particle size of the microcapsules is from about 1 to 2 μm.

The wall-forming polymeric material may be a polyacrylate, a polymethacrylate, a cellulose ether or ester, or a combination thereof. In certain embodiments, the polymer is a polymethacrylate, more preferably poly(methyl methacrylate) co-methacrylic acid (herein referred to sometimes as PMMA) or ammonium methacrylate copolymer type B (poly(ethyl acrylate)-co-(methyl methacrylate)-co-(trimethylammonium-ethyl methacrylate chloride), also known as Eudragit RSPO® or EuRSPO®). In other certain embodiments, the polymer is a cellulose ether or ester such as, but not limited to, methyl cellulose, ethyl cellulose, hydroxypropyl methyl cellulose, hydroxypropyl cellulose, cellulose acetate, cellulose acetate phthalate, or hydroxypropyl methyl cellulose acetate phthalate. In other certain embodiments, the wall-forming polymeric material is a combination of the mentioned polymers such as, but not limited to, combinations of Eudragit RSPO® with either PMMA or ethyl cellulose (EC). The amount (weight/weight) of the polymers from the total microcapsule weight varies according to the polymer and the presence of additives and can be within a range selected from about 2 to about 50%, about 2 to about 40%, about 2 to about 30%, or about 2 to about 25%, preferably about 2%, 5%, 10% or 25%, by weight.

In certain embodiments of the invention, the microcapsules contain no additives. For example, see hereinafter in Example 5 (Table 7—samples 260411L and 250111L), wherein the black pigment is black iron oxide in an amount of about 90% or 95%, by weight, and the wall-forming material is ammonium methacrylate copolymer type B in an amount of about 5% or 10%, by weight.

The microcapsules of the invention may further comprise one or more additives including, but not limited to, mineral oils such as paraffin oil, mineral oil substitutes such as hydrogenated polyisobutene, or castor oil, lanolin, butylene glycol cocoate or carnauba wax. In certain embodiments, the amount of additive is within a range selected from about 5 to about 50%, about 5 to about 40%, about 5 to about 30%, or about 10 to about 25%, preferably about 10% or 25%. In certain embodiments, the additive is hydrogenated polyisobutene used, for example, in Example 2 (Table 1) and in Example 5 (Table 7—sample 270411L). In other certain embodiments, the additive is butylene glycol cocoate used, for example, in Example 3 (Table 5).

In certain embodiments, the black pigment is carbon black in an amount of about 50%, by weight, the wall-forming material is poly(methyl methacrylate) co-methacrylic acid in an amount of about 25%, by weight, and the additive is hydrogenated polyisobutene, in an amount of about 25%, by weight (see Example 2 (Table 1)). In other certain embodiments, the black pigment is carbon black in an amount of about 90%, by weight, the wall-forming material is poly(methyl methacrylate) co-methacrylic acid in an amount of about 2%, by weight, and the additive is butylene glycol cocoate, in an amount of about 10%, by weight (see Example 3 (Table 5)). In certain embodiments the black pigment is black iron oxide in an amount of about 80%, by weight, the wall-forming material is ammonium methacrylate copolymer type B in an amount of about 10%, by weight, and the additive is hydrogenated polyisobutene in an amount of about 10%, by weight (see Example 5 (Table 7 sample 270411L)).

When the black pigments are mixed with an oily substance it results in a richer color. Thus, the wetting agent hydrogenated polyisobutene or butylene glycol cocoate provides a more intense black color.

The microcapsules of the present invention including carbon black microcapsules or black iron oxide microcapsules as free flowing powder or in slurry/paste form, contain high purity grade black pigments designed to provide intense black color in cosmetic formulations for full color development.

The advantages of the microcapsules of the present invention include:
  (i) High loading (90% for both carbon black and black iron oxide).
  (ii) Available in both powder form and slurry/paste form.
  (iii) Strong color strength.
  (iv) No agglomerates.
  (v) Less clumping, less beading and less buildup.
  (vi) Better formulation stability.
  (vii) Reduced micro problems.
  (viii) Better handling, ease of use and reduced dusting problems.
  (ix) More uniformity as well as narrower particle size distribution.
  (x) No nano issue—average particle size of 1-2 micron or 40 micron.
  (xi) Enhanced waterproof properties of the final formulation.
  (xii) Can be used in mascaras, eyeliners and other water based products as well as in waterproof mascaras.

In another aspect the present invention provides a method for the preparation of the microcapsules comprising a black pigment described above, the method comprising:
  a) preparing an organic solution of a black pigment with the wall-forming polymeric material in ethyl acetate, optionally in the presence of one or more additives, and subjecting the solution to homogenization or low shear mixing/stirring until a homogenate suspension is obtained;
  b) mixing said homogenate suspension with an aqueous solution containing an emulsifier, under either low or high shear stirring, to form an emulsion;
  c) adding to the emulsion formed in (b) an excess amount of water to initiate extraction of the organic solvent from the emulsion, thus obtaining microcapsules;
  d) optionally allowing sedimentation of the microcapsules; and
  e) isolating said microcapsules of c) or d) by filtration, subsequently washing with water or with 10% alcohol, and optionally drying the wet capsules.

Figure 1A:
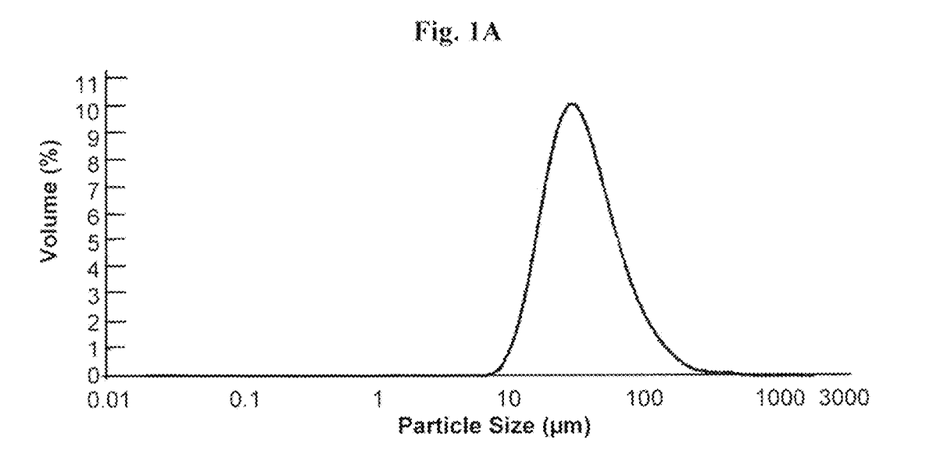
FIGS. 1A-1B show particle size distribution of carbon black microcapsules having an average particle size of 40 µm or 1-2 µm, respectively.
Figure 1B:
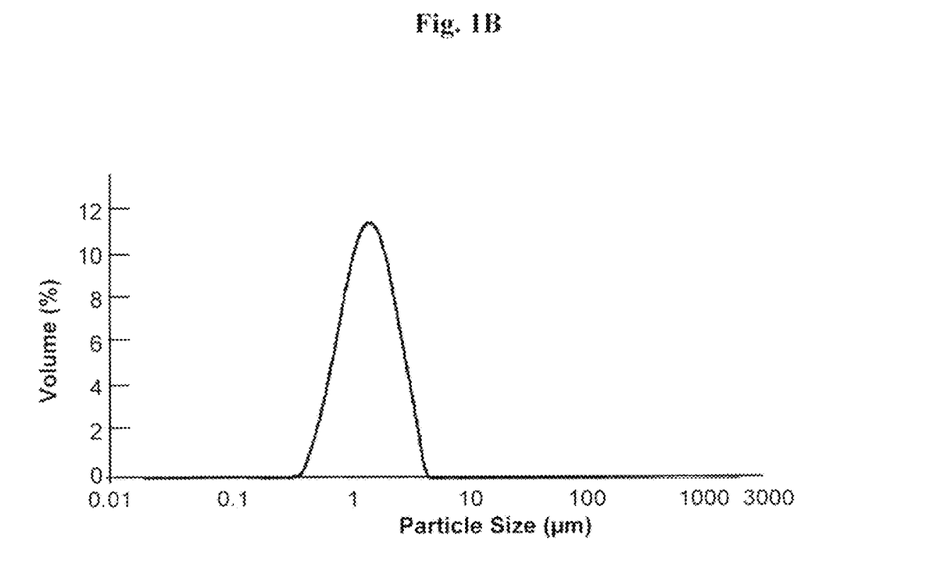

According to the method of the present invention it is possible to control the average particle size of the microencapsulated black pigment by performing step b) of the above method either at low or high shear stirring. The term "low shear stirring" or "low shear mixing" or "low shear mixing/stirring" refers to a mixing of about 300-600 revolutions per minute (RPM), preferably about 400 RPM, and provides bigger microcapsules. The term "high shear stirring" refers to a mixing at about 6000-12000 RPM, preferably about 6000-8000 RPM, and provides smaller microcapsules. For example, black pigment microcapsules having an average particle size of 40 μm were obtained under stirring at 400 RPM as shown in Example 2 (step 2.2) and FIG. 1A, while smaller microcapsules, i.e. having an average particle size of 1-2 μm, were obtained under stirring at 6000-8000 RPM as shown in Example 3 (step 3.2) and FIG. 1B.

The homogenization of the organic phase ("master batch") is an important stage in the process for preparation of the microcapsules comprising a black pigment. However, for the preparation of carbon black microcapsules, the duration of this stage should be no longer than 5 min. In addition, for the preparation of carbon black microcapsules, the duration of the emulsion stage is also short (5 min). Longer emulsion times result in a cream which can not be mixed.

In another aspect the present invention provides compositions/formulations comprising microencapsulated carbon black, black iron oxide, or a mixture thereof. In certain embodiments the compositions/formulations of the invention comprise microcapsules selected from: (i) carbon black microcapsules; (ii) black iron oxide microcapsules, (iii) microcapsules comprising a mixture of black iron oxide and carbon black, or (iv) a mixture of black iron oxide microcapsules and carbon black microcapsules, preferably 3% of carbon black microcapsules and 7% of black iron oxide microcapsules.

These compositions/formulations are particularly for cosmetic use and include, for example, mascara, eyeliner, eye shadow, lipstick, blush, makeup, cream concealer, and foundation for makeup formulations. In some preferred embodiments, the invention provides mascara formulations comprising microencapsulated carbon black and/or iron oxide black (see Examples 6 and 7).

The preparation of the formulation can be carried out by mixing the black pigment microcapsules with the other ingredients of the formulation and compressing the mixture, wherein the other ingredients of the formulation may optionally be heated to obtain a homogeneous solution, and cooled prior to the addition of the black pigment microcapsules (as exemplified in Example 6).

The invention will now be illustrated by the following non-limiting Examples.

EXAMPLES

Materials

The following materials used in the examples are listed with their abbreviations used herein and their suppliers: carbon black (amorphous, D&C Black#2, Amerilure Inc, USA); black iron oxide (amorphous, Sun Chemical, USA); poly(ethyl acrylate)-co-(methyl methacrylate)-co-(trimethylammonium-ethyl methacrylate chloride) (Eudragit RSPO® or EuRSPO®, Evonik, Germany); poly(methyl methacrylate) co-methacrylic acid (PMMA; average MW ca. 15,000; Sigma-Aldrich); hydrogenated polyisobutene (JEEN International Corporation, USA or Elementis UK Ltd, Germany); ethyl acetate (Sciencelab.com, Inc., USA); polyvinyl alcohol (PVA 4%; Kuraray America, Inc., USA); butylene glycol cocoate (Gattefosse, France).

Example 1. General Procedure for Preparation of Microcapsules Containing a Black Pigment The microcapsules are prepared by the solvent removal method comprising:

a) preparing an organic solution of the black pigment with a wall-forming polymeric material selected from a acrylate, a polymethacrylate, a cellulose ether, or a combination thereof, in ethyl acetate, optionally with one or more additives such as wetting agents, and homogenizing or low shear mixing/stirring until a homogenate suspension is obtained;

b) mixing said homogenate suspension with an aqueous solution containing an emulsifier, under low or high shear stirring, to form an emulsion;

c) adding to the formed emulsion an excess amount of water to initiate extraction of the organic solvent from the emulsion, thus obtaining microcapsules;

d) optionally leaving for a time sufficient to allow sedimentation of the microcapsules; and e) isolating said microcapsules by filtration, subsequently washing with water or with 10% alcohol (to remove ethyl acetate residues) and optionally drying the wet microcapsules.

Example 2. Preparation of Microcapsules Containing Carbon Black 2.1 Preparation of Organic Phase ("Master Batch"):

An organic phase (herein called "master batch" (MB)) was prepared by gradually adding 25 g of the wall-forming polymer poly(methyl methacrylate-co-methacrylic acid), under stirring, into 566.7 g of ethyl acetate, heating to 50° C. and stirring well until the mixture was homogeneous (about 10 min). The polymer solution was cooled to 25° C. The wetting agent hydrogenated polyisobutene (25 g) was added to this mixture and it was further stirred for about 10 min. Carbon black pigment was then gradually added to the mixture and it was stirred for 1 min. The mixture was then homogenized for 2 min to obtain a homogenate suspension (composition detailed in Table 1).

TABLE 1

Organic phase (MB) composition

| | Material | Loading component of MB (g)-(for 100 g) |
|---|---|---|
| 1 | poly(methyl methacrylate-co-methacrylic acid) | 25 |
| 2 | Hydrogenated Polyisobutene | 25 |
| 3 | Carbon Black pigment | 50 |
| 4 | Ethyl Acetate | 566.7 (removed) |

2.2 Preparation of the Emulsion:

A water solution was prepared by mixing tap water (2400 g) with polyvinyl alcohol (PVA, Mowiol® 4-88, Kuraray Specialities Europe (KSE) GmbH, Frankfurt am Main, Germany; 4%, 160 g) such that the water phase consisted of 0.25% PVA. Ethyl acetate (106.7 g) was added to the water phase under stirring at 400 RPM for 10 min. The master batch of step 2.1 above (666.7 g) was gradually added into the ethyl acetate/water emulsion under stirring at 400 RPM, and further stirred for additional 1 min (composition detailed in Table 2).

TABLE 2

Emulsion composition

| | Material | Loading for 100 g portion (g) |
|---|---|---|
| 1 | Tap Water | 2400 |
| 2 | PVA Mowiol 4-88, KSE solution 4% | 160 |
| 3 | Ethyl Acetate | 106.7 |
| 4 | MB | 666.7 |

2.3 Procedure of Extraction:

The extraction phase was composed of 13600 g tap water. The emulsion of step 2.2 (3333 g) above was gradually added into the extraction phase under stirring at 130 RPM and was further stirred for additional 15 min (composition detailed in Table 3).

TABLE 3

Extraction content

| | Material | Loading for 100 g portion (g) |
|---|---|---|
| 1 | Tap Water | 13600 |
| 2 | Emulsion | 3333 |

2.4 Washing and Drying Procedure:

The microcapsules of step 2.3 above were separated by filtration as a "cake". The "cake" was washed on a filter paper under vacuum with tap water (1 L) followed by deionized water (0.2 L) to obtain a wet "cake" with 50-60% water content. The "cake" of microcapsules was then dried in a vacuum drying oven under Silica Gel (500 g) for 48 hr, vacuum 30 mbar, temperature ~40° C. The dry capsules were sifted with an automatic sifter for 10 min.

The mean particle size of the obtained carbon black microcapsules was 34 μm (see FIG. 1). The yield of production of encapsulated carbon black was 90%. The bulk density of the microencapsulated carbon black was higher than that of the raw material in both loose and packed forms (see Table 4).

TABLE 4

Bulk density microencapsulated black iron oxide vs raw material

| | Loose g/cm$^3$ | Packed g/cm$^3$ |
|---|---|---|
| Carbon Black-Raw material | 0.20 | 0.22 |
| CarbonCap1-Capsules | 0.31 | 0.38 |

Example 3. Preparation of Microcapsules Containing a High Percentage of Carbon Black Pigment 3.1 Preparation of Master Batch:

A master batch was prepared by gradually adding 2 g of the wall-forming polymer poly(methyl methacrylate-co-methacrylic acid), under stirring, into 566.7 g of ethyl acetate, heating to 50° C. and stirring well until the mixture was homogeneous (about 10 min). The polymer solution was cooled to 25° C. Butylene glycol cocoate (10 g) was added to the polymer solution and it was further stirred for about 10 min. Carbon black pigment (88 gr) was then gradually added to the mixture and it was stirred for 1 min. The mixture was then homogenized for 2 min to obtain a homogenate suspension (composition detailed in Table 5).

TABLE 5

MB composition with high loading of carbon black

| | Material | Loading component of MB (g)-(for 100 g) |
|---|---|---|
| 1 | poly(methyl methacrylate-co-methacrylic acid) | 2 |
| 2 | Butylene glycol cocoate | 10 |
| 3 | Carbon Black pigment | 88 |
| 4 | Ethyl Acetate | 566.7 |

3.2 Preparation of the Emulsion:

A water solution was prepared by mixing tap water (2400 g) with polyvinyl alcohol (PVA, Mowiol® 4-88, KSE GmbH, Frankfurt am Main, Germany; 4%, 160 g) such that the water phase consisted of 0.25% PVA. Ethyl acetate (106.7 g) was added to the water phase under stirring at 6000-8000 RPM for 10 min. The master batch of step 3.1 above (666.7 g) was gradually added into the ethyl acetate/water emulsion under stirring at 6000-8000 RPM, and further stirred for additional 1 min (composition detailed in Table 6).

TABLE 6

Emulsion composition

| | Material | Loading for 100 g portion (g) |
|---|---|---|
| 1 | Tap Water | 2400 |
| 2 | PVA Mowiol 4-88, KSE solution 4% | 160 |
| 3 | Ethyl Acetate | 106.7 |
| 4 | MB of 3.1 | 666.7 |

The extraction, washing and drying procedures are identical to the extraction, washing and drying procedures described above in 2.3 and 2.4 of Example 2.

Figure 2A:
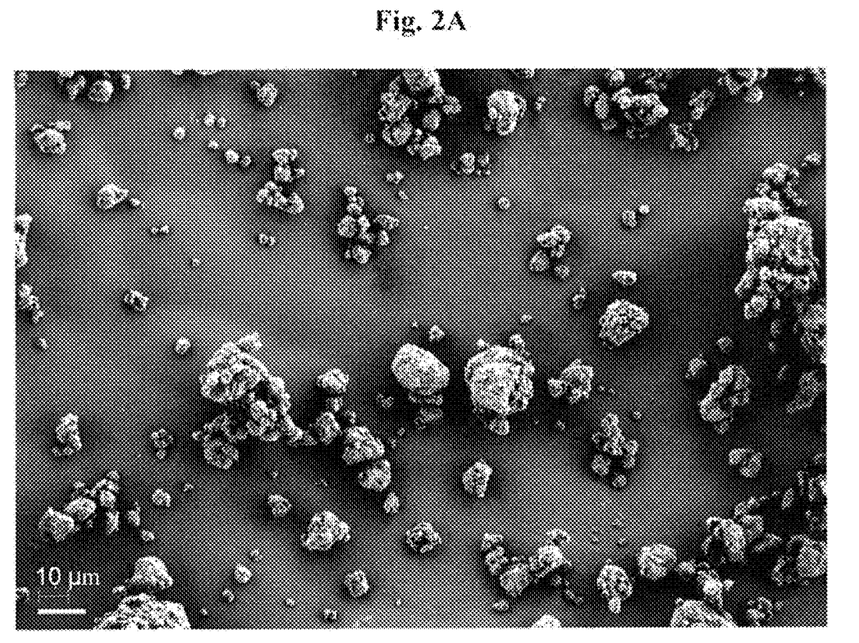
FIGS. 2A-2C show scanning electron microscope (SEM) images of non-encapsulated carbon black (raw material, FIG. 2A); carbon black microcapsules having an average particle size of 40 µm in magnification ×1000 (FIG. 2B), and carbon black microcapsules having an average particle size of 1-2 µm in magnification of ×5000 (FIG. 2C).
Figure 2B:
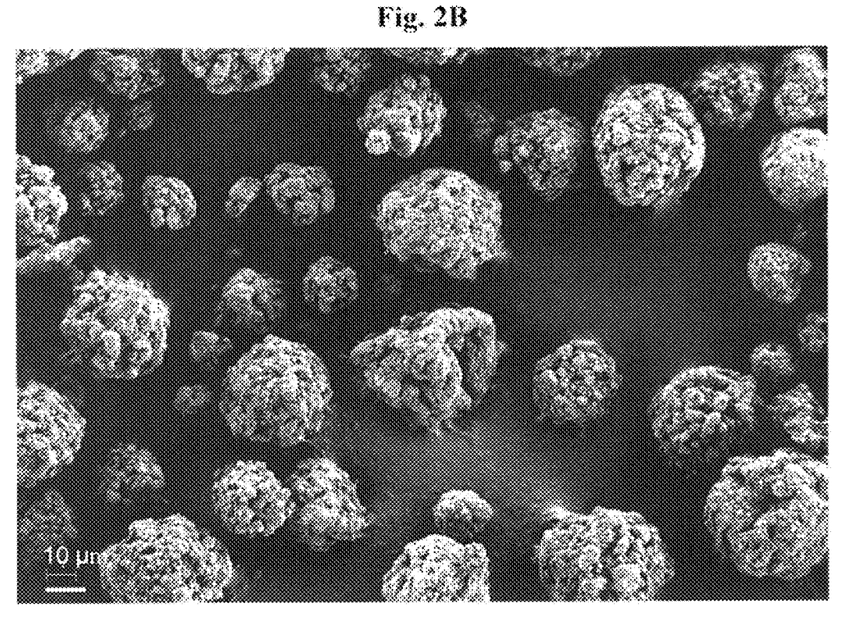
Figure 2C:
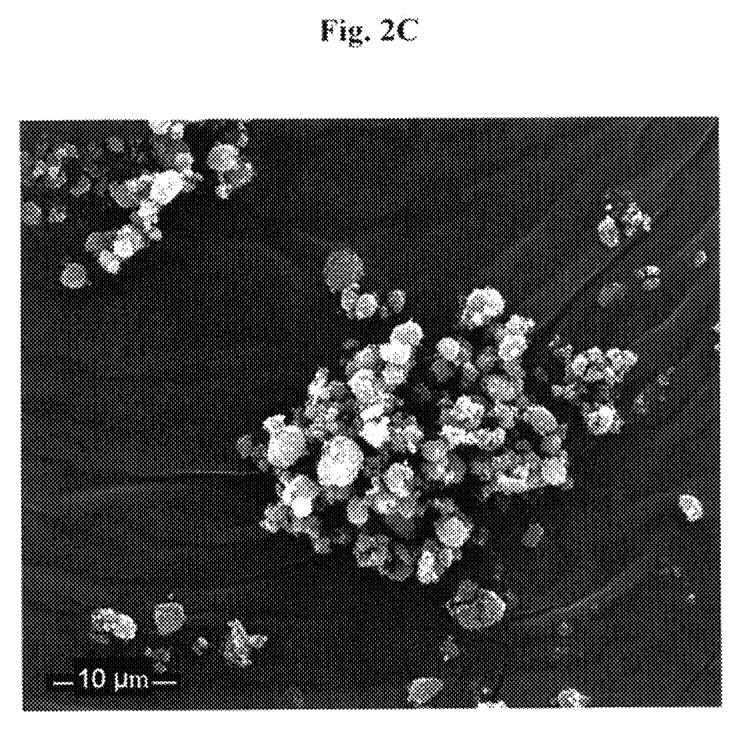

Example 4. Scanning Electron Microscopy Images of the Carbon Black Microcapsules Scanning electron microscopy (SEM) images of carbon black (raw material) and the carbon black microcapsules prepared as detailed above in Example 2 or Example 3 were taken using Zeiss Ultra Gemini® (Zeiss, Germany, FIGS. 2A-2C). The SEM image of the microcapsules shows that the microcapsules have an indeterminate form (FIG. 2B).

Example 5. Preparation of Microcapsules Containing Black Iron Oxide 5.1 Preparation of Organic Phase ("Master Batch"):

An organic phase was prepared by gradually adding 10 g of the wall-forming polymer ammonium methacrylate copolymer type B (EuRSPO®), under stirring, into 122.2 g of ethyl acetate, until the mixture was homogeneous (about 10 min). The wetting agent hydrogenated polyisobutene (10 g) was added to this mixture and it was further stirred for about 10 min. Black iron oxide (80 gr) was then gradually added to the mixture and it was further stirred for 1 min. The mixture was then homogenized for 7 min to obtain a homogenate suspension (composition detailed in Table 7).

TABLE 7

MB (organic phase) composition

| | | Loading component of MB for 100 g portion (g) | | |
|---|---|---|---|---|
| No | Raw material | BlackM Cap 270411L | BlackM Cap 260411L | BlackM Cap 250111L |
| 1 | Black Iron Oxide | 80 | 95 | 90 |
| 2 | EuRSPO (ammonium methacrylate copolymer type B) | 10 | 5 | 10 |
| 3 | Hydrogenated Polyisobutene | 10 | — | — |
| 4 | Ethyl Acetate | 122.2 (removed) | | |

5.2 Preparation of the Emulsion:

A water solution was prepared by mixing tap water (562.5 g) with polyvinyl alcohol (PVA, Mowiol® 4-88, KSE GmbH, Frankfurt am Main, Germany; 4%, 37.5 g) such that the water phase consisted of 0.25% PVA. Ethyl acetate (66.7 g) was added to the water phase under stirring at 400 RPM for 10 min. The master batch of step 5.1 above (235.8 gr) was gradually added into the ethyl acetate/water emulsion under stirring at 400 RPM, and further stirred for additional 7 min (composition detailed in Table 8).

TABLE 8

Emulsion composition

| | Material | Loading for 100 g portion (g) |
|---|---|---|
| 1 | Tap Water | 562.5 |
| 2 | PVA Mowiol 4-88, KSE solution 4% | 37.5 |
| 3 | Ethyl Acetate | 66.7 |
| 4 | MB | 235.8 |

5.3 Procedure of Extraction:

The extraction phase was composed of 3933 g tap water. The emulsion of step 5.2 above (902.5 gr) was gradually added into the extraction phase under stirring at 130 RPM and was further stirred for additional 15 min (composition detailed in Table 9).

TABLE 9

Extraction content

| | Material | Loading for 100 g portion (g) |
|---|---|---|
| 1 | Tap Water | 3933 |
| 2 | Emulsion | 902.5 |

5.4 Washing and Drying Procedure:

The microcapsules of step 5.3 above were separated by filtration as a "cake". The "cake" was washed on a filter paper under vacuum with tap water (0.5 L) to obtain a wet "cake" with 50-60% water content. The "cake" of microcapsules was then dried in a vacuum drying oven under Silica Gel (500 g) for 48 hr, vacuum 30 mbar, temperature ~40° C. The dry capsules were sifted with an automatic sifter for 10 min.

Figure 3:
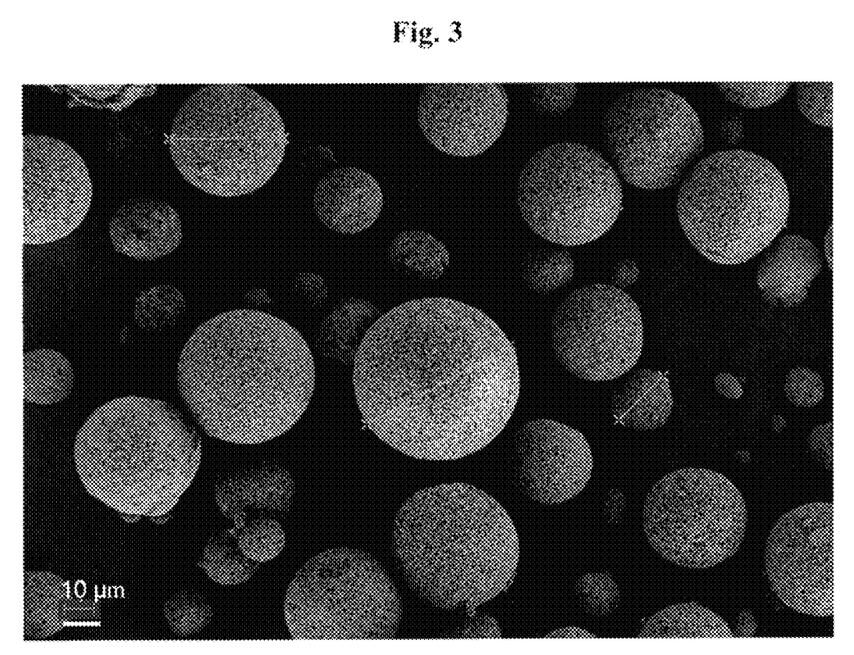
FIG. 3 shows SEM image of black iron oxide microcapsules in magnification ×1000.

Scanning electron microscopy (SEM) images of the black iron oxide microcapsules taken using Zeiss Ultra Gemini® (Zeiss, Germany), show that the microcapsules have a spherical form with single nucleus (FIG. 3). The yield of production was 85 to 91% (BlackM Cap 270411L—89%; BlackM Cap 260411L—91%; and Black Cap Inner production—85%, see Table 7). The bulk density of the microencapsulated black iron oxide was similar to that of the raw material in the loose form and lower than that of the raw material in the packed form (see Table 10).

TABLE 10

Bulk density microencapsulated black iron oxide vs raw material

| No | Samples | Loose g/cm$^3$ | Packed g/cm$^3$ |
|---|---|---|---|
| 1 | Black Iron Oxide-raw material | 0.7 | 1.1 |
| 2 | BlackM Cap-270411L | 0.64 | 0.75 |
| 3 | BlackM Cap 260411L | 0.68 | 0.77 |
| 4 | BlackM Cap 250111L | 0.55 | 0.65 |

Example 6. Preparation of Mascara Oil in Water Formulation

Mascara formulations were prepared using the ingredients listed in Table 11 below, as follows: Phase 1 was prepared by mixing the water with a marine or anchor propeller at 800-1200 RPM, dispersing a thixotropic agent Thickagent LC™ (xanthan gum & hectorite & cellulose; Les Colorants, France) at room temperature till complete dispersion was achieved. Heating to 75° C. with mixing, adding Euxyl® PE 9010 (a liquid cosmetic preservative based on phenoxyethanol and ethylhexylglycerin; Shulke, Norderstedt Germany), and triethanolamine (TEA; Gadot, Israel) till pH is 7.2-7.4 and the gel viscosity decreases. Phase 2 was prepared by mixing all the ingredients while heating to 75° C. Phase 3 was prepared by mixing Covacryl E-14™ and Covacryl E-15™ (acrylate film formers and texturisers; Les Colorants, France) and Phenonip® (a liquid preservative; Sharon Laboratories, Israel), and heating to 50-55° C. Phase 2 was added to phase 1 under mixing with marine/anchor propeller at 800-1200 RPM at 75° C. The mixing was continued for additional 10 min followed by cooling to 55° C. Phase 3 was added to the combined phases 1+2 while mixing for 10 min at 55° C., followed by cooling to room temperature. 4-10% of the microencapsulated black pigment can be incorporated to the above formulation at the end of the formulation preparation using either low or high shear mixing.

TABLE 11

Ingredients for mascara formulation containing carbon black microencapsules

| Ingredient | % (weight) |
|---|---|
| Phase 1 | |
| Water | 48.67 |
| Thickagent LC ™ (Xanthan gum & Hectorite & Cellulose) | 0.45 |
| Euxyl ® PE 9010 (Phenoxyethanol and Ethylhexylglycerin) | 1 |
| Triethanolamine | 0.3 |
| Phase 2 | |
| Base RW 135 (Synthetic beeswax & Carnauba & Stearic acid & Ceteareth 25 & PEG-2 stearate & Paraffinum liquidum & Hydrogenated coconut oil & Cethyl alcohol; Les Colorants, France) | 15.125 |
| Dimethicone 350 (dimethyl-bis(trimethylsilyloxy)silane; Dow) | 1.505 |
| Phase 3 | |
| Covacryl E-14 ™ (acrylates copolymer, Les Colorants, France) | 11 |
| Covacryl E-15 ™ (acrylates copolymer, Les Colorants, France) | 22 |
| Phenonip ® (Sharon Labs, Israel) | 0.65 |
| Phase 4 | |
| Microencapsulated black pigment | 4-10% |

Example 7. Preparation of Eye Liner Formulations

Eye liner formulations were prepared by using the ingredients listed in Table 12, as follows: Phase 1 was prepared by mixing the water with a marine propeller at 800-1200 RPM, dispersing at room temperature Thickagent LC™, followed by addition of glycerin (Gadot, Israel), ethylenediaminetetraacetic acid (EDTA; Sigma-Aldrich), Dermacryl LT™ (National Starch, USA) and Euxyl® PE 9010 and heating the phase to 75° C. Phase 2 was prepared by mixing all the ingredients and heating to 75° C. Phase 2 was poured into phase 1 followed by homogenization of the combined phases by high shear homogenizer for 10 min at 75° C. The mixing was continued while cooling the mixture to 50° C. Ingredients of Phase 3 were gradually added and the mixture/formulation was cooled to room temperature. 4-10% of the microencapsulated black pigment was incorporated to the above formulation at the end of the formulation preparation using either low or high shear mixing.

TABLE 12

Ingredients for eye liner formulation containing microencapsulated black pigment

| Ingredient | % (weight) |
|---|---|
| Phase 1 | |
| Water | 83.812 |
| Thickagent LC ™ | 0.3 |
| Glycerin | 3.45 |
| Ethylenediaminetetraacetic acid (EDTA) | 0.81 |
| Dermacryl LT ™ (acrylates/octylacrylamide copolymer) | 2.3 |
| Euxyl ® PE 9010 | 1 |
| Phase 2 | |
| Performa V ®825 polymer (hyper-branched polyalphaolefin) (New Phase technologies, USA) | 1.15 |
| Carnauba wax (Zifroni, Israel) | 0.128 |
| Candellila wax (Zifroni, Israel) | 1.05 |
| Laurex ® C16 (linear alcohols) (Croda, UK) | 0.65 |
| Stearic acid TP (Croda, UK) | 1.05 |
| Ozokerite (Zifroni, Israel) | 0.5 |
| Phase 3 | |
| Silicone Dow Corning ®-556 (phenyl trimethicone) | 1.15 |
| Zoharsyl L-30 (sodium lauroyl sarcosinate, Zohar-Dalia, Israel) | 2.875 |
| Phenonip ® | 0.575 |
| Phase 4 | |
| Microencapsulated black pigments | 4-10 |

The invention claimed is:

1. Monolayered microcapsules having a mean particle size within a range selected from about 1 to about 100 μm, the microcapsules comprising a single core of a black pigment which is carbon black or a mixture of carbon black and black iron oxide, and a shell of a wall-forming polymeric material selected from poly(methyl methacrylate)-co-methacrylic acid, ammonium methacrylate copolymer type B, a cellulose ether, a cellulose ester, or a combination thereof, wherein the microcapsules do not contain a plasticizer, and further comprise one or more additives selected from the group consisting of hydrogenated polyisobutene and butylene glycol cocoate, and wherein the microcapsules have a black color,
wherein the black pigment is carbon black, and the amount of carbon black in the microcapsules is within a range selected from about 80 to about 90% of the total weight of the microcapsules, or wherein the black pigment is a mixture of carbon black and black iron oxide, the ratio between the carbon black and black iron oxide in said mixture is in a range of from 1:20 to 20:1, respectively, and said black pigment is in an amount from about 80 to about 90% of the total weight of the microcapsules.

2. The microcapsules according to claim 1, wherein said microcapsules have a mean particle size within a range of from about 1 to about 90 μm, about 1 to about 80 μm, about 1 to about 70 μm, 1 about to about 60 μm, about 1 to about 50 μm, about 30 to about 50 μm, about 34 to about 40 μm, about 1 to about 40 μm, about 1 to about 30 μm, about 1 to about 20 μm, about 1 to about 10 μm, about 1 to about 5 μm, or about 1 to about 3 μm.

3. The microcapsules according to claim 1, wherein said wall-forming material is poly(methyl methacrylate) co-methacrylic acid, ammonium methacrylate copolymer type B, cellulose ethyl ether, cellulose ethyl ester, or a combination thereof.

4. The microcapsules according to claim 3, wherein the wall-forming material is poly(methyl methacrylate) co-methacrylic acid or ammonium methacrylate copolymer type B and the amount of the polymer in the microcapsules is at least 2% of the total weight of the microcapsules.

5. The microcapsules according to claim 1, wherein the black pigment is carbon black in an amount of at least 81% of the total weight of the microcapsules, the wall-forming material is poly(methyl methacrylate) co-methacrylic acid in an amount of about 2% of the total weight of the microcapsules, and the additive is butylene glycol cocoate, in an amount of about 10% of the total weight of the microcapsules.

6. A method for the preparation of microcapsules according to claim 1, comprising:
   a) preparing an organic solution of a black pigment with the wall-forming polymeric material in ethyl acetate, in the presence of said one or more additives, and subjecting the solution to homogenization or low shear mixing/stirring until a homogenate suspension is obtained;
   b) mixing said homogenate suspension with an aqueous solution containing an emulsifier, under low or high shear stirring, to form an emulsion;
   c) adding to the emulsion formed in (b) an excess amount of water to initiate extraction of the organic solvent from the emulsion, thus obtaining microcapsules;
   d) optionally allowing sedimentation of the microcapsules; and
   e) isolating said microcapsules of c) or d) by filtration, subsequently washing with water or with 10% alcohol, and optionally drying the wet capsules.

7. The method according to claim 6, wherein said low shear stirring in step a) or step b) ranges from 300 to 600 revolutions per minute (RPM); and said high shear stirring in step b) ranges from 6000 to 12000 RPM.

8. The method according to claim 6, wherein the wall-forming polymeric material is poly(methyl methacrylate) co-methacrylic acid, ammonium methacrylate copolymer type B, cellulose ethyl ether, cellulose ethyl ester, or a combination thereof.

9. The method according to claim 6, wherein the steps of homogenization or mixing/stirring in step a) and stirring in step b) are carried out for no longer than 5 minutes.

10. A cosmetic formulation comprising black pigment microcapsules according to claim 1.

11. The cosmetic formulation according to claim 10, which is a mascara, an eyeliner, an eye shadow, a lipstick, a blush, a makeup, a cream concealer, or a foundation for makeup formulation.

12. The cosmetic formulation according to claim 10, prepared by mixing the black pigment microcapsules with the other ingredients of the formulation and compressing the mixture.

13. Monolayered microcapsules having a mean particle size within a range selected from about 1 to about 100 μm, the microcapsules comprising a single core of a black pigment which is carbon black, and a shell of a wall-forming polymeric material selected from a polyacrylate, a polymethacrylate, a cellulose ether, a cellulose ester, or a combination thereof, wherein the microcapsules do not contain a plasticizer, and wherein the microcapsules have a black color, wherein the amount of carbon black in the microcapsules is within a range of from 80% to 90% of the total weight of the microcapsules, and wherein the microcapsules further comprise one or more additives selected from the group consisting of hydrogenated polyisobutene and butylene glycol cocoate.

14. Monolayered microcapsules having a mean particle size within a range selected from about 1 to about 100 μm, the microcapsules comprising a single core of a black pigment which is carbon black, and a shell of a wall-forming polymeric material, wherein the microcapsules do not contain a plasticizer, and wherein the microcapsules have a black color, wherein the amount of carbon black in the microcapsules is at least 81% of the total weight of the microcapsules, the wall-forming material is poly(methyl methacrylate) co-methacrylic acid in an amount of about 2% of the total weight of the microcapsules, and the microcapsules further comprise an additive which is butylene glycol cocoate, in an amount of about 10% of the total weight of the microcapsules.

\* \* \* \* \*